United States Patent [19]

Dyke et al.

[11] Patent Number: 4,831,039
[45] Date of Patent: May 16, 1989

[54] ISOQUINOLINE COMPOUND

[75] Inventors: Stanley F. Dyke, Kenmore, Australia; Gordon H. Phillipps, Wembley, United Kingdom

[73] Assignee: Glaxo Group Limited, London, England

[21] Appl. No.: 129,064

[22] Filed: Dec. 7, 1987

Related U.S. Application Data

[63] Continuation of Ser. No. 938,845, Dec. 8, 1986, abandoned, which is a continuation of Ser. No. 548,842, Nov. 4, 1983, abandoned.

[30] Foreign Application Priority Data

Nov. 4, 1982 [GB] United Kingdom ................ 8231540

[51] Int. Cl.$^4$ ...................... A61K 31/47; C07D 471/04
[52] U.S. Cl. ........................................ 514/283; 546/42
[58] Field of Search ........................... 546/42; 514/283

[56] References Cited

U.S. PATENT DOCUMENTS 4,042,591  8/1977  Kaul ..................................... 546/42
4,434,290  2/1984  Bisagni et al. ........................ 546/70
4,444,776  4/1984  Bisagni et al. ....................... 514/287

FOREIGN PATENT DOCUMENTS 0161102  11/1985  European Pat. Off. ............ 514/283
2129799   5/1984  United Kingdom .................. 546/42

OTHER PUBLICATIONS

Dainis, Chemical Abstracts, vol. 77, 88260h (1972).
Spray, PhD Thesis, University of Bath, England (1980).
Affonso et al., Chemical Abstracts, vol. 75, 143961y (1971).
Kato et al., Chemical Abstracts, vol. 83, 152267u (1975).
Uchida et al., J. Heterocyclic Chem., vol. 15, pp. 1303–1307 (1978).
Kasai et al., Chemical Abstracts, vol. 83, 168484y (1975).
Kishi et al., Chemical Abstracts, vol. 92, 75895d (1980).

*Primary Examiner*—Nicholas S. Rizzo
*Assistant Examiner*—Diana G. Rivers
*Attorney, Agent, or Firm*—Bacon & Thomas

[57] ABSTRACT

5,14-Dihydrobenz[5,6]isoindolo[2,1-b]isoquinoline-8,13-dione

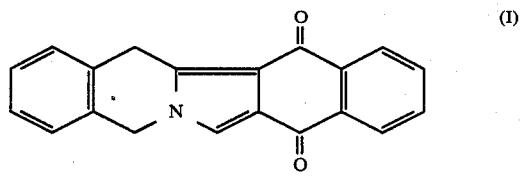

(I)

exhibits anticancer activity. The compound can be prepared by reaction of 2-formyl-3-carboxyl-1,2,3,4-tetrahydroisoquinoline with 1,4-naphthoquinone and is particularly suitably administered parenterally in microcrystalline suspension form.

9 Claims, No Drawings

ISOQUINOLINE COMPOUND

This application is a continuation, of application Ser. No. 938,845 filed Dec. 8, 1986, now abandoned, which is a continuation of Ser. No. 548,842, filed Nov. 4, 1983 and now abandoned.

This invention relates to a new isoquinoline compound, useful in the treatment of cancers.

We have found that the novel compound 5,14-dihydrobenz [5,6] isoindolo [2,1-b] isoquinoline-8,13-dione possesses activity useful in the treatment of cancers.

According to one aspect of the invention we thus provide the compound formula I

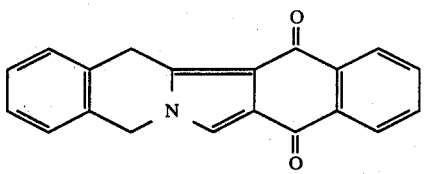

including, individually or in admixture, allomorphs and/or tautomers thereof.

The compound of the invention exists in at least two crystalline forms, and both forms of the compound are included within the scope of the invention. The two crystalline forms which have been isolated have been shown by powder X-ray crystallography to be morphologically distinct and exhibit different IR spectra. These two forms are referred to herein as forms A and B and may be distinguished, inter alia, by the significantly higher solubility in dimethylformamide of Form B.

According to a further aspect of the invention we provide a process for the preparation of a compound of formula I, which process comprises reacting 2-formyl-3-carboxy-1,2,3,4-tetrahydroisoquinoline with 1,4-napthoquinone under carboxyl activating conditions.

Thus, for example, the process may be carried out in the presence of an alkanoic acid anhydride, such as acetic acid anhydride, optionally in the presence of a solvent, e.g. a hydrocarbon solvent such as toluene. Preferably, the process is carried out with heating at for example 80°–120° C.

Recrystallization of the initial product of process, which is normally in Form B if the reaction is carred out in the absence of an additional solvent, e.g. from chloroform and methylene chloride, yields the compound of the invention in Form A. Furthermore, Form A can also be obtained from Form B by heating as a slurry in toluene, preferably in the presence of a seed crystal of Form A.

The compound of the invention is also obtained in Form B by dissolving it in a liquid solvent e.g. dimethylformamide, and dispersing the solution into a second liquid miscible with the first solvent, e.g. water, in which the compound of the invention is substantially insoluble. If the solution of the compound of formula I is rapidly dispersed in the second liquid the compound is precipitated out of solution in a finely divided, e.g. microcrystalline, form.

According to a further aspect of the invention we thus provide a process for the preparation of a compound of formula I in microcrystalline form wherein a compound of formula I dissolved in a liquid solvent therefor is rapidly dispersed in a second liquid which is miscible with the said liquid solvent and in which the compound of formula I is substantially insoluble.

The compound of formula I possesses anticancer activity, particularly against tumours such as sarcomas, carcinomas and hepatomas.

Thus, when the compound is adminstered intraperitoneally or intravenously to mice with a subcutaneous tumour arising from an implant of S180 cells, subsequent examination has shown that tumour growth has been significantly reduced and in some cases total regression of the tumour has occured. Activities against hepatoma (D23 Rat Solid Tumour), HT29 Human Colon Xenograft in Nude Mice, and L 1210 (Mouse lymphocytic leukaemia, grown ascitally) have also been shown.

According to a further aspect of the present invention we therefore provide a compound of formula I as defined above for use in the treatment of the human or animal body to combat cancer, particularly tumours, therein.

According to a yet further aspect of the present invention we provide the use of a compound of formula I as defined above for the treatment of the human or animal body to combat cancer, particularly tumours, therein.

According to a still further aspect of the present invention we provide a method of treatment of the human or animal body to combat cancers, particularly tumours, therein, which method comprises administering to the said body an effective amount of a compound of formula I as defined herein.

According to a yet still further feature of the present invention we provide a pharmaceutical composition comprising as active ingredient a compound of formula I as defined above together with one or more pharmaceutical carriers or excipients.

For pharmaceutical administration the compound of general formula I may be incorporated into conventional preparations in either solid or liquid form.

The compositions may, for example, be presented in a form suitable for oral, rectal, topical or, more preferably, parenteral administration. Suitable forms include, for example, tablets, capsules, granules, suppositories, creams, ointments and lotions and more particularly suspensions and/or solutions for injection or infusion.

The active ingredient may be incorporated in excipients customarily employed in pharmaceutical compositions such as, for example, talc, gum arabic, lactose, starch, magnesium sterarate, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of the compound of the invention. Suitable dosage units for adults contain from 50 to 1000 mg of the compound of the invention. The dosage, which may be varied according to the particular patient to be treated and complaint concerned, may, for example, be from 0.25 to 7.0 g in a day in adults.

In view of the substantial insolubility of the compound of formula I in water, a particularly preferred form for administration is that of a suspension of the compound in microcrystalline form. The microcrystalline compound of formula I may be in either Form A or Form B or may be a mixture of both and preferably has a mean particle size not greater than 2 microns.

Especially advantageous parenteral administration forms of the compound of the invention can be prepared in suspension form for administration either as an injection or by infusion.

For injection the compound of formula I is conveniently present in a micro-crystalline form with mean particle size in the order of 1 to 2 microns (hereinafter referred to as "the microfine form") dispersed in water for injections.

For the infusion preparation the compound of formula I is conveniently present in a microcrystalline form with a mean particle size in the order of half a micron (hereinafter referred to as "the ultrafine form")- dispersed in water for injections.

To prepare either of the microfine or ultrafine suspensions, a solution of the compound of formula I in a solvent such as dimethylformamide, optionally containing a surfactant, is slowly added with rapid dispersion into a miscible non solvent, e.g. water. Suitable surfactants include a lecithin or a sorbitan derivative e.g. polysorbate 80 BP. For the preparation of the microfine material the dimethylformamide solution is preferably dispersed in an equal volume of non solvent e.g. water. Ultrafine material is conveniently prepared by dispersing the dimethyl formamide solution in approximately three or more volumes of water. The dimethylformamide may be removed from the resultant suspensions by conventional techniques such as dialysis or a method involving ultrafiltration.

The microfine crystalline suspension is such that the particles will separate on centrifugation or even on standing; the crystalline material can thus be collected and resuspended at a higher concentration.

By the use of such techniques for preparing the suspensions, the microfine presentation conveniently has a concentration of 5 mg/ml, and the ultrafine of 1 mg/ml.

The invention is further illustrated by the following Examples.

EXAMPLE 1

Preparation of 5,14-dihydrobenz[5,6,]isoindolo[2,1-b]isoquinoline-8,13-dione

A mixture of 2-formyl-3-carboxy-1,2,3,4-tetrahydroisoquinoline (17.50g) and 1,4-naphthoquinone (26.95 g) in acetic anhydride (437 ml) was heated at 100° C. with stirring for 30 min. The reaction mixture was cooled and the solid collected by filtration, washed with ether and dried.

Recrystallisation from chloroform/methylene chloride gave the title compound in Form A (11.13 g), λmax (ethanol) 245 ($\epsilon$43,700), 265 ($\epsilon$14,100) and 368 nm ($\epsilon$5,200).

The infra-red spectrum of the title compound in Form A as a mull in mineral oil exhibited characteristic peaks at 1756 (shoulder), 1748, 1598, 1572, 1546 and 838 cm$^{-1}$.

EXAMPLE 2

Preparation of 5,14-dihydrobenz[5,6]isoindolo[2,1-b]isoquinoline 8,13-dione

A mixture of 2-formyl-3-carboxy-1,2,3,4-tetrahydroisoquinoline (20 g) and 1,4-naphthoquinone (30.8 g) in acetic anhydride (500 ml) was heated at 100° C. with stirring for 30 minutes. The reaction mixture was cooled, the solid collected by filtration, washed with acetic anhydride (50 g) with ether (2 × 100ml) and dried to give the title compound in Form B (26 g).

Analysis found: C, 80.4; H, 4.3; N, 4.7 ($C_{20}H_{13}NO_2$ requires: C, 80.2; H, 4.3; N, 4.6%).

The infra-red spectrum of the title compound in Form B as a mull in mineral oil exhibited characteristic peaks at 1766, 1742, 1594, 1564, 1544 and 1292 cm$^{-1}$.

EXAMPLE 3

Microfine suspension for parenteral administration

| | |
|---|---|
| Active Ingredient | up to 800 mg |
| Dimethylformamide or dimethylacetamide | 200 ml |
| Polysorbate 80 BP | 200 mg |
| Water for injections | 200 ml |

The active ingredient and polysorbate 80 are dissolved in the solvent which is then added to the water with vigorous mixing thus producing a fine precipitate.

The solvent is then removed by dialysis or methods involving ultrafiltration. Alternatively, the crystals are separated by centrifugation and resuspended in water for injections, preferably containing polysorbate 80 BP. Sodium chloride is then added to render the product isotonic. The final product has the following composition:

| | % w/v |
|---|---|
| Active ingredient (microfine form) | 0.1 to 5 |
| Polysorbate 80 BP | 0.1–0.05 |
| Sodium chloride | 0.9 |
| Water for injections | to 100 |

The sodium chloride may if desired be replaced with other agents such as dextrose (5%), glycerol (2.5%) or sorbitol (5%).

EXAMPLE 4

Ultrafine suspension for parenteral administration

| | |
|---|---|
| Active ingredient | up to 800 mg |
| Dimethylformamide AR | 200 ml |
| Polysorbate 80 BP | 400 mg |
| Water for injections | 600 ml |

The active ingredient is dissolved in the dimethylformamide. The polysorbate 80 is dissolved in the water and the active ingredient/dimethylformamide is then added to the water with vigorous mixing. An ultrafine suspension is thus produced. The dimethylformamide is then removed from the product by a process involving ultrafiltration or by dialysis.

Glycerol is then added to render the product isotonic. The final product has the following composition:

| | % w/v |
|---|---|
| Active ingredient (ultrafine form) | up to 0.1 |
| Polysorbate 80 BP | ≦0.05 |
| Glycerol | 2.5 |
| Water for injections | to 100 |

The glycerol may, if desired, be replaced with other agents such as dextrose (5%) or sorbitol (5%).

EXAMPLE 5

Ultrafine suspension for parenteral administration 18.5 mg of the active ingredient is dissolved in 5 ml of dimethylformamide at ambient temperature to give solution (A). Solution (B) is made by dispersing 0.185 g of soy bean lecithin in 18.5 ml of distilled water and sonicating with a Dawes Soniprobe for 1½ , minutes under nitrogen in an icebath. Solution (A) is added to solution (B) whilst agitating with a paddle stirrer. The dimethylformamide is removed by dialysis or a method involving ultrafiltration. Glycerol is then added to render the product isotonic.

EXAMPLE 6

Ultrafine suspension for parenteral administration 37 mg of the active ingredient and 37 mg of soya bean lecithin are dissolved in 10 ml of dimethylformamide. To this solution is added 37 ml of distilled water whilst agitating with a paddle stirrer or a magnetic stirrer. The dimethylformamide is removed by dialysis or a method involving ultrafiltration. Glycerol is then added to render the product isotonic.

We claim:
1. The compound of formula I

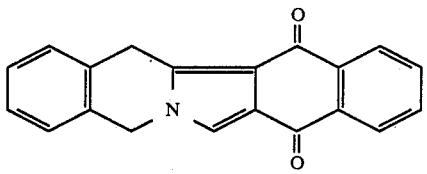

including, individually or in admixture, allomorphs and/or tautomers thereof.

2. A compound as claimed in crystalline claim 1 in Form A.

3. A compound as claimed in crystalline claim 1 in Form B.

4. A compound as claimed in claim 1 in a finely divided, microcrystalline form.

5. A compound as claimed in claim 4 in which the microcrystalline particles have a mean particle size of 1 to 2 microns.

6. A compound as claimed in claim 4 in which the microcrystalline particles have a mean particle size of the order of 0.5 microns.

7. A pharmaceutical composition comprising as an active ingredient a compound as claimed in claim 1 together with one or more pharmaceutical carriers or excipients.

8. A pharmaceutical composition as claimed in claim 7 in dosage unit form comprising from 50 to 1000 mg of the active ingredient per dosage unit.

9. A pharmaceutical composition as claimed in claim 7 in injectable form.

* * * * *